United States Patent [19]

Pebler

[11] 4,005,001
[45] Jan. 25, 1977

[54] COMBUSTIBLES SENSOR

[75] Inventor: Alfred R. Pebler, Pittsburgh, Pa.

[73] Assignee: Westinghouse Electric Corporation, Pittsburgh, Pa.

[22] Filed: Mar. 27, 1973

[21] Appl. No.: 345,393

[52] U.S. Cl. .............................. 204/195 S; 204/1 T; 324/30 R; 324/29

[51] Int. Cl.[2] ..................................... G01N 27/46

[58] Field of Search .......... 204/195 S, 1 T; 324/29, 324/33

[56] References Cited

UNITED STATES PATENTS

| | | | |
|---|---|---|---|
| 3,400,054 | 9/1968 | Ruka et al. | 204/1 T |
| 3,558,280 | 1/1971 | Panson et al. | 23/254 |
| 3,698,955 | 10/1972 | Lilly et al. | 204/195 S X |
| 3,719,564 | 3/1973 | Lilly et al. | 204/1 T |

Primary Examiner—G. L. Kaplan
Attorney, Agent, or Firm—Michael P. Lynch

[57] ABSTRACT

A gaseous mixture of oxygen and fuel (combustibles) is supplied to first and second electrodes disposed on opposite surfaces of an oxygen ion conductive solid electrolyte member wherein the electrodes are composed of different materials each exhibiting a different catalytic action on the gaseous mixture at a given temperature. The difference in oxygen potentials established at the respective electrodes as a result of the dissimilar catalytic action produces oxygen ion conductivity in the solid electrolyte cell which produces an electrical signal the magnitude of which is indicative of the combustible present in the mixture, i.e., methane, hydrogen, carbon monoxide, etc.

3 Claims, 7 Drawing Figures

COMBUSTIBLES SENSOR

BACKGROUND OF THE INVENTION

Commercially available combustion meters generally employ a temperature sensor that monitors the heat effect from the catalytic-heterogeneous combustion of fuels with excess oxygen. Most commonly used is the hot wire technique, which employes a resistance heated noble metal filament commonly made of platinum. If the filament is heated in an atmosphere containing fuels and sufficient oxygen for combustion is present, the oxidation of the fuels is catalyzed at the metal-gas interface. The heat released by the combustion raises the temperature of the wire and thereby also increases the resistance. Typically the wire forms one leg of an electrical bridge configuration with an identical reference wire located in a fuel free atmosphere. The imbalance of the bridge circuit resulting from heating of the filament produces a measurement of the fuel concentration.

The disadvantage of hot wire detector is its relatively low sensitivity which limits the usefulness for monitoring low fuel concentrations, i.e., less than one percent.

SUMMARY OF THE INVENTION

The following decription in connection with the accompanying drawings illustrates a technique utilizing an oxygen ion conductive solid electrolyte cell to determine the presence of specific combustible constituents within a gaseous mixture containing oxygen. The oxygen potential difference established at the electrodes of the solid electrolyte cell resulting from dissimilar catalytic action on the oxygen and combustibles at a given temperature is interpreted as an indication of the type of combustibles present. The oxygen demand at the respective electrodes for a given combustible constituent is a function of the electrode material and the temperature. A typical electrode combination would that of platinum and gold where at a specific operating temperature the platinum electrode may exhibit greater catalytic activity than the gold electrode and the EMF produced as a result of the difference in oxygen potential at the respective electrodes is indicative of the fuel constituent present in the mixture.

Suitable electrode compositions and combinations include either gold or silver as one electrode with the second electrode being a group VIII metal such as platinum, palladium and rhodium.

It has been determined experimentally that for a given set of electrodes the optimum electrochemical cell response to various fuel constituents is a function of temperature. Therefore it is possible to identify the presence of various fuel constituents within an oxygen containing mixture by cycling the electrochemical cell through a range of operating temperatures and recording the signal generated by the electrochemical cell through the range of temperatures. The presence of various fuel constituents within the mixture will be manifested by a significant electrochemical cell output signal at the operating temperature considered optimum for the various fuel constituents.

Inasmuch as the operating temperature of the solid electrolyte cell is typically between 400 and 1000° C, the selection of electrode material is somewhat limited. Electrodes composed of platinum or palladium in combination with electrodes composed of a noble metal have proven to be satisfactory.

DESCRIPTION OF THE DRAWINGS

The invention will become more readily apparent from the following examplary description in connection with the accompanying drawings.

DESCRIPTION OF THE PREFERRED EMBODIMENT

Figure 1:
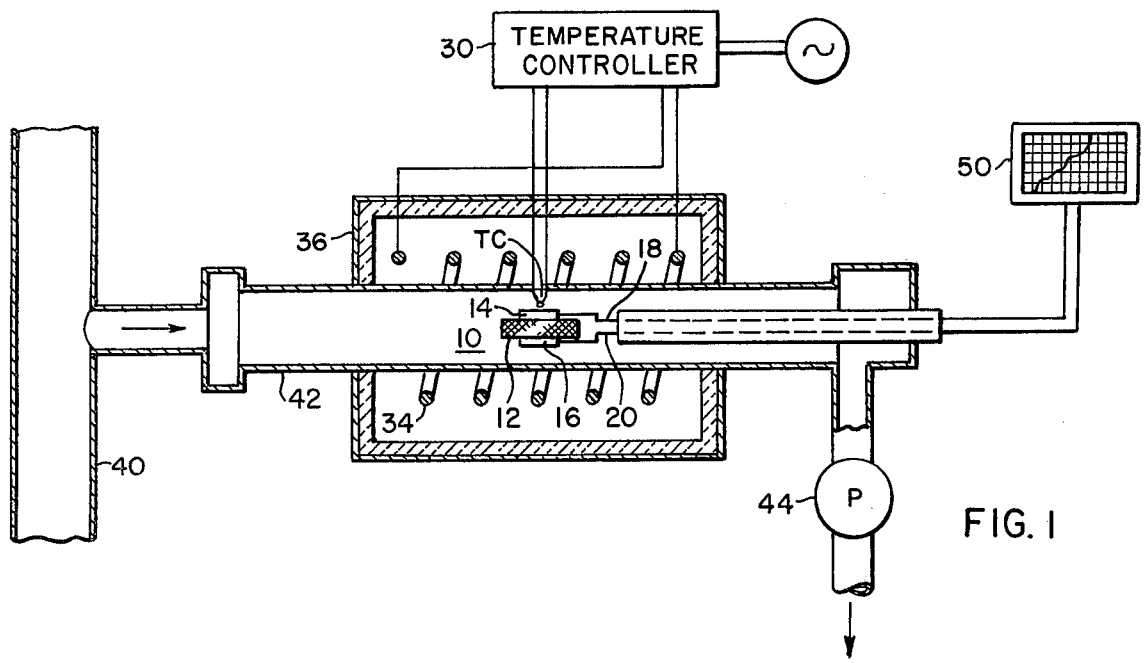
FIG. 1 is a schematic illustration of a typical embodiment of the invention.

Referring to FIG. 1 there is illustrated schematically a combustibles sensor 10 comprised of a solid electrolyte electrochemical cell 12 in the form of a disk having electrodes 14 and 16 disposed on opposite surfaces thereof with electrical lead members 18 and 20 extending therefrom. Temperature control circuit 30 is operatively connected to the heater element 34 of the furnace member 36 to control the temperature of the combustibles sensor 10 to a desired operating temperature in a range beetweem 400° C and 1000° C.

In the embodiment illustrated in FIG. 1 a flow of the gaseous mixture present in the furnace stack 40 is drawn through the gas flow conduit 42 by the pump 44 for intimate contact with the combustibles sensor 10 prior to exhausting to the atmosphere.

The solid electrolyte member 12 is of a type exhibiting significant oxygen ion conductivity in response to a difference in oxygen potential at the electrodes 14 and 16 and generating an EMF output signal which is transmitted to a signal measuring circuit 50 by the lead wires 18 and 20. The basic operation of the oxygen ion conductive solid electrolyte electrochemical cell and the various material compositions of the solid electrolyte member is described in detail in U.S. Pat. No. 3,400,054 issued Sept. 3, 1968 and assigned to the assignee of the present invention. A typical commercially available oxygen ion conductive solid electrolyte is a calcium stabilized zirconia composition represent as $ZrO_2 \cdot 15$ mol% CaO.

While the embodiment of the combustibles sensor system of FIG. 1 is illustrated as including a combustible sensor positioned within a furnace assembly, a more compact combination of the furnace assembly and combustibles sensor for in situ gas monitoring applications could be designed utilizing the teachings of U.S. Pat. No. 3,546,086, issued Dec. 8, 1970 and assigned to the assignee of the present invention. This latter U.S. Pat. discloses the use of an internally heated solid electrolyte electrochemical cell assembly thus eliminating the need for an external furnace assembly.

The conversion of the conventional solid electrolyte oxygen measuring device to a combustibles sensor is achieved through the use of material compositions for electrodes 14 and 16 which exhibit different catalytic reactivity relative to the oxygen and combustibles constituents of the gaseous mixture. The catalytic reactivity characteristic of a material corresponds to its capability of adsorbing fuel and oxygen to support a catalytic action on the surface of the electrode material and a capability of subsequently releasing the by-products of the reaction to permit further catalytic action without poisoning the material with the by-products of the reaction.

The operating temperature of the combustibles sensor is a significant factor inasmuch as too low a temperature will not initiate the necessary catalytic reactivity required to provide suitable sensor response to the constituents of the gas mixture, while too high an operating temperature will result in too rapid a response at the respective electrodes thus minimizing the oxygen potential difference across the cell which as indicated above is the basis for determining the combustible constituents within gaseous mixture.

Figure 4:
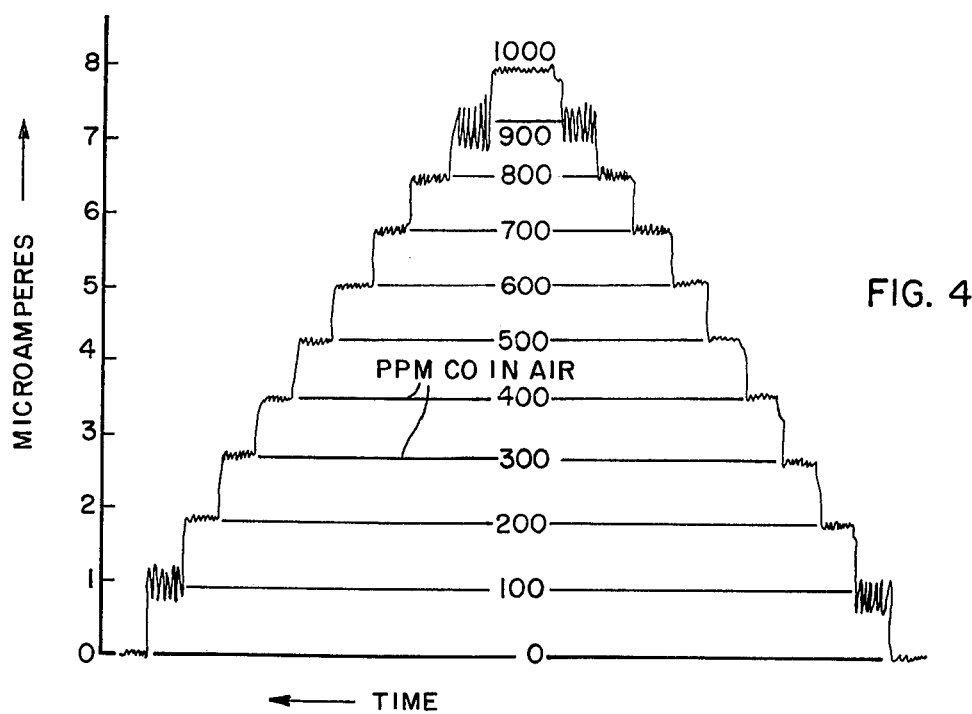
FIG. 4 is a graphical illustration of the current produced by the embodiment of FIG. 1 for various concentrations of carbon monoxide in air.

The high sensitivity exhibited by the combustibles sensor in response to carbon monoxide is shown by the current trace in FIG. 4. The carbon monoxide concentration was varied in step increments first in an increasing direction and then in a decreasing direction. The apparent noise at the high and low dilutions was concluded to be the result of incomplete mixing of the carbon monoxide and air and the graphical representations reflect true variations in the carbon monoxide concentration. In addition to the reliable reproducibility of the combustibles sensor, the graphical representation of FIG. 4 further illustrates the fast response of the combustibles sensor to changes in fuel concentrations.

A suitable range of operating temperatures for the anticipated combustibles constituents has been experimentally determined to be between 400 and 1000° C. At these relatively high operating temperatures the selection of the electrode material for electrodes 14 and 16 is limited to materials that can withstand the elevated operating temperature. It has been determined experimentally that the noble metals, such as gold and silver, provide desirable catalytic activity and when paired with an electrode composed of platinum or palladium provide sufficient oxygen potential difference to produce an EMF signal indicative of combustibles content of the gas mixture.

The response characteristics of a combustibles sensor comprised of a calcium stabilized zirconia solid electrolyte and electrodes of platinum and gold are graphically illustrated in FIGS. 2 through 5.

Figure 2:
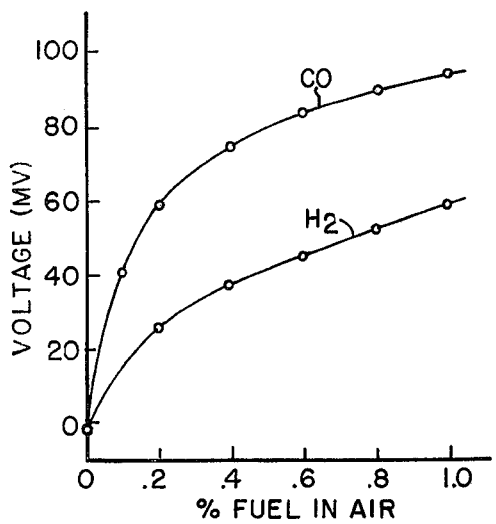
FIG. 2 is a graphic illustration of the response of the embodiment of the invention of FIG. 1 to gaseous mixtures as a function of the fuel concentration.

The graph of FIG. 2 reflects the open cell EMF produced by the combustibles sensor for varying concentrations of carbon monoxide and hydrogen.

Figure 3:
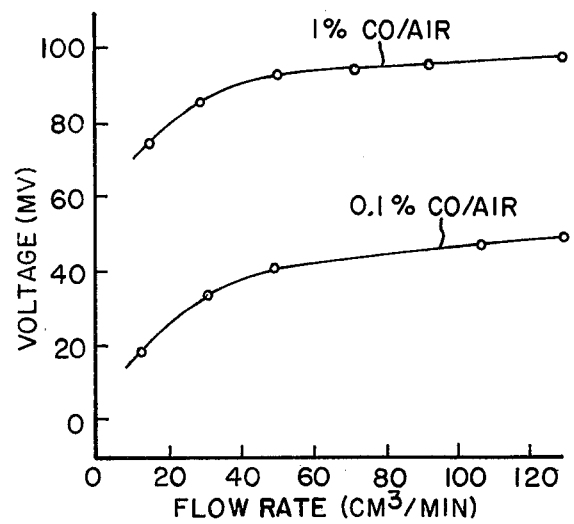
FIG. 3 is a graphic illustration of the response of the embodiment of FIG. 1 as a function of the slow rate of the gaseous mixture.

The graphical representation of FIG. 3 illustrates the flow rate sensitivity of the combustibles sensor for two concentrations of carbon monoxide in air. It is apparent from FIG. 3 that the flow rate established by pump 44 of FIG. 1 should be maintain above a minimum value of 50 cubic centimeters per minute in order to minimize the variation in the combustibles sensor output signal as a function of gas flow rate.

A plot of the output signal of the combustibles sensor 10 utilizing a combination of a gold electrode and a platinum electrode for incremental changes in carbon monoxide content in air at an operating temperature of 735° C is illustrated in FIG. 4.

Electrical output signals produced by the combustibles sensor 10 in response to differences in oxygen potential established at the respective electrodes as a result of the difference in catalytic reactivity of the respective electrodes can be measured in terms of current (microamperes) or voltage (millivolts). A plot of the output signal of the combustibles sensor operating in the current mode is illustrated graphically in FIG. 5. The reliable reproducibility of the output signal of the combustibles sensor 10 is apparent from FIG. 5.

It is essential for the proper operation of the combustibles sensor that an excess oxygen condition exist in the gaseous mixture in order to assure the presence of an oxygen potential at each of the electrodes following the catalytic reaction between the combustibles constituents and the oxygen at the electrode surfaces. The excess oxygen condition can be defined as the presence of an amount of oxygen in excess of that required to completely combust the combustible constituent in the gaseous mixture. It has been experimentally observed under excess oxygen conditions that significantly high combustibles sensor output potentials are developed across a solid electrolyte member having a platinum electrode and a gold electrode disposed on opposite surfaces in response to the present of small amounts (less than 1%) of hydrogen, carbon monoxide and methane in operating temperatures between 500° and 800° C.

Figure 6:
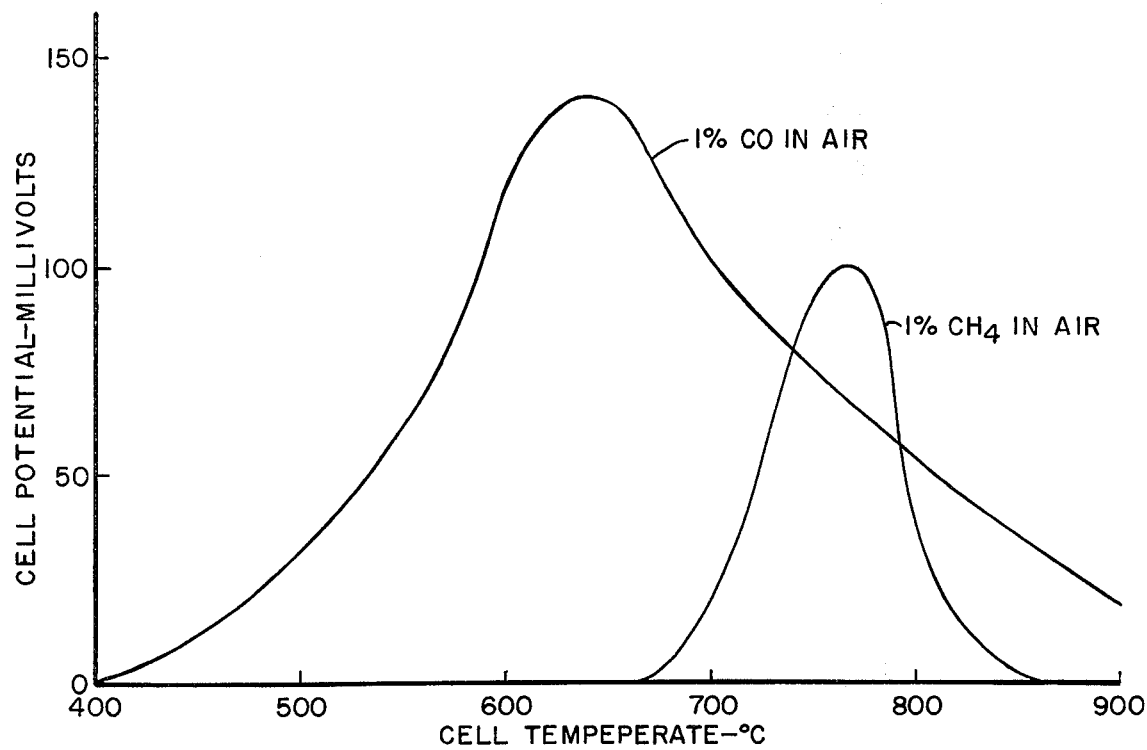
FIG. 6 is a graphical illustration of the response of the embodiment of FIG. 1 to various fuel constituents as a function of temperature.

It has been further determined experimentally, as illustrated in FIG. 6 that different combustible constituents produce peak output signals at different operating temperature. This realization permits the utilization of a single combustible sensor of the type described above operating over a range of temperatures, as provided by temperature controller 30, to analyze a gas mixture and identify, or display as on recorder 50 of FIG. 1, in accordance with the information illustrated in FIG. 6 the presence of various combustible constituents within the gas mixture.

It is also of interest to note that while a typical embodiment as illustrated in FIG. 1 requires a temperature sensing device, such as a thermocouple TC, to monitor the operating temperature and provide a signal back to the temperature controller 30, the temperature sensor TC can be eliminated when the combustibles sensor utilizes an electrode combination, such as platinum and gold, which functions to produce a thermoelectric potential which is proportional to the operating temperature. The platinum-gold electrode combination in effect functions as a thermocouple thus permitting the electrode to function in a dual capacity to both provide an oxygen potential difference indicative of the combustibles constituent as well as providing an electrical signal indicative of the operating temperature.

Continuing the discussion of the combustibles sensor relative to a typical configuration utilizing a calcium stabilized zirconia electrolyte 12 and electrode 14 composed of gold and electrode 16 composed of platinum, the observed operational characteristics of the combustibles sensor can be explained by the different activity by which the platinum and gold electrodes catalyze the combustion of fuels and excess oxygen within a gas mixture. Platinum is known to completely combust fuel at a temperature of approximately 600° C while the reaction on the gold electrode at this temperature is kinetically hindered. Hence, the difference in demand for oxygen at the respective electrodes gives rise to a difference in the oxygen potential as measured across the solid electrolyte member 12. This agrees with the observation that the platinum electrode is positive, corresponding to the anodic reaction

followed by the reaction at the surface

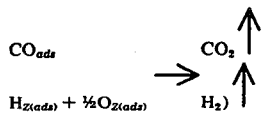

where □ represents empty lattice sites in the cubic stabilized zirconia, and (ads) means absorbed.

The combustion takes place among adsorbed species and $CO_{(ads)}$, $H_{2(ads)}$ and $O_{2(ads)}$ represent CO, $H_2$ and $O_2$ adsorbed on the electrode.

Figure 7:
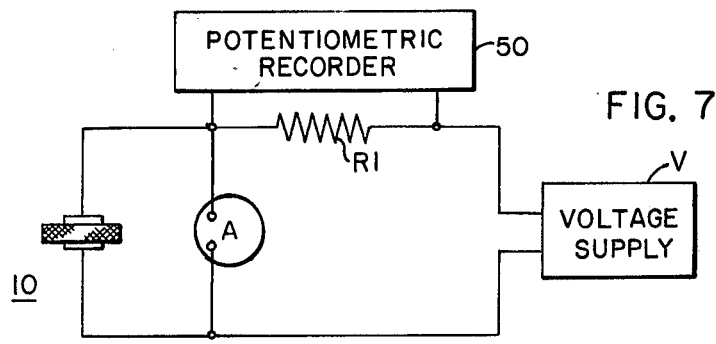

While the embodiment illustrated in FIG. 1 depicts a voltage mode of operation of the combustibles sensor there is illustrated schematically in FIG. 7 a current mode of operation of the combustibles sensor 10. The output of the combustibles sensor 10 is supplied to a resistive load Rl and the current is recorded as the voltage drop across the load Rl by the potentiomeric recorder PR. The thermoelectric potential is compensated by an external voltage supply V. In the absence of fuel or combustibles present in the gas mixture, no potential difference other than that arising from the thermoelectric potential of the goldplatinum combination is developed. This potential is accounted for as will be explained with reference to FIG. 7.

The presence of combustible within the gas mixture contacting the electrodes of the combustibles sensor 10 produces an additional potential difference between the electrodes of a polarity opposite to the thermoelectric potential. The potential difference developed as a result of combustibles present in the gas mixture offsets the applied compensating voltage provided by the electronically stabilized low impedance voltage source V and results in a current flow through the load resistor Rl of FIG. 7.

Figure 5:
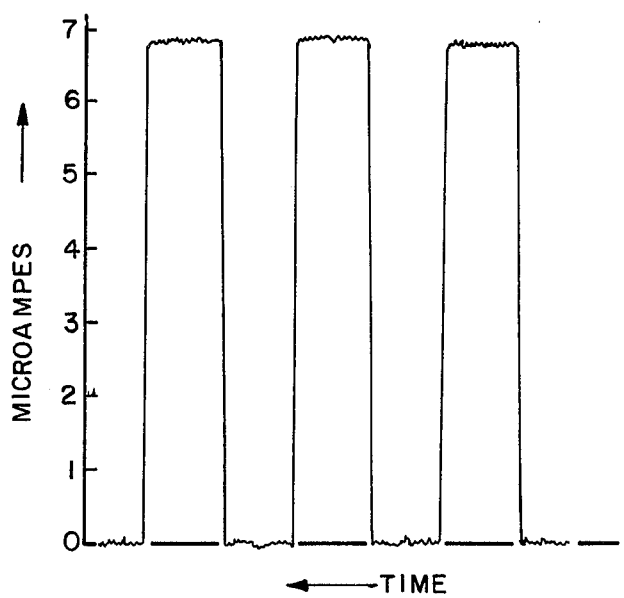
FIG. 5 is a graphical illustration of the reproducibility of the output signals of the embodiment of FIG. 1.

The output signal information from the combustibles sensor 10 illustrated graphically in FIG. 5, was obtained with 1000 ppm carbon monoxide in air. Initially pure air was passed over the electrodes of the combustibles sensor. A thermoelectric potential of approximately 4.45 millivolts corresponding to an operating temperature of approximately 660° C was compensated for by the voltage source V of FIG. 7. under the pure air conditions the current flow was zero. At point A of FIG. 5, 1000 ppm of carbon monoxide was added to the air flow over the electrodes of the combustibles sensor. As seen in the graphical representation of FIG. 5 the current rapidly reached a stable value. At point B of the graphical representations of FIG. 5, the combustibles sensor was again subjected to a pure air mixture resulting in a rapid drop of current flow.

I claim:

1. Apparatus for determining the presence of predetermined combustible constituents such as methane, hydrogen and carbon monoxide, in an excess oxygen gas mixture, comprising, an oxygen ion conductive solid electrolyte electrochemical cell including a first and second electrode means disposed on opposite surfaces thereof, means adapted for supplying an excess oxygen gas mixture containing one or more combustible constituents simultaneously to said first and second electrodes, said first electrode composed of a material for supporting a first rate of catalytic combustion reactivity between said oxygen and combustible constituents of said mixture and said second electrode composed of a material exhibiting a second rate of catalytic combustion reactivity between said oxygen and combustible constituents of said gas mixture, said first rate of catalytic combustion reactivity being different than said second rate of catalytic combustion reactivity so as to produce an oxygen potential difference between said first and second electrodes, said solid electrolyte electrochemical cell developing an output signal corresponding to said oxygen potential difference, said output signal being indicative of the combustible constituents present in said gas mixture, said oxygen potential difference produced by said combustible constituents being a function of the temperature of said solid electrolyte electrochemical cell and each particular combustible constituent producing a maximum oxygen potential difference at a predetermined temperature, and means for maintaining said solid electrolyte electrochemical cell at the predetermined temperature at which maximum oxygen potential difference is produced by a combustible constituent of interest.

2. Apparatus for determining the presence of predetermined combustible constituents such as methane, hydrogen and carbon monoxide, in an excess oxygen gas mixture, comprising, an oxygen ion conductive solid electrolyte electrochemical cell including a first and second electrode means disposed on opposite surfaces thereof, means adapted for supplying an excess oxygen gas mixture containing one or more combustible constituents simultaneously to said first and second electrodes, said first electrode composed of a material for supporting a first rate of catalytic combustion reactivity between said oxygen and combustible constituents of said mixture and said second electrode composed of a material exhibiting a second rate of catalytic combustion reactivity between said oxygen and combustible constituents of said gas mixture, said first rate of catalytic combustion reactivity being different than said second rate of catalytic combustion reactivity so as to produce an oxygen potential difference between said first and second electrodes, said solid electrolyte electrochemical cell developing an output signal corresponding to said oxygen potential difference, said output signal being indicative of the combustible constituents present in said gas mixture, said oxygen potential difference produced by said combustible constituents being a function of the temperature of the solid electrolyte electrochemical cell and each particular combustion constituent producing a maximum oxygen potential difference at a predetermined temperature, means for heating said solid electrolyte electrochemical cell over a range of said predetermined temperatures, and means for monitoring the output signals developed at said predetermined temperatures to determine the presence of particular combustible constituents.

3. Apparatus as claimed in claim 2 wherein said first and second electrodes combine to produce a thermoelectric potential which is indicative of the temperature of the solid electrolyte electrochemical cell.

* * * * *